United States Patent [19]

Barth

[11] 4,427,678

[45] Jan. 24, 1984

[54] 6-AMINOMETHYLPENICILLANIC ACID 1,1-DIOXIDE DERIVATIVES AS BETA-LACTAMASE INHIBITORS

[75] Inventor: Wayne E. Barth, East Lyme, Conn.

[73] Assignee: Pfizer Inc., New York, N.Y.

[21] Appl. No.: 388,323

[22] Filed: Jun. 14, 1982

Related U.S. Application Data

[63] Continuation-in-part of Ser. No. 338,797, Jan. 11, 1982, abandoned.

[51] Int. Cl.$^3$ .................. A61K 31/545; A61K 31/43; C07D 499/00
[52] U.S. Cl. .............................. 424/246; 260/245.2 R; 424/263; 424/271
[58] Field of Search ................. 260/245.2 R; 424/246, 424/271, 263

[56] References Cited

U.S. PATENT DOCUMENTS

| | | | |
|---|---|---|---|
| 4,207,323 | 6/1980 | Beattie et al. | 424/270 |
| 4,234,579 | 3/1979 | Barth | 424/246 |
| 4,237,051 | 2/1980 | McCombie | 260/245.2 R |
| 4,287,181 | 9/1981 | Kellogg | 424/114 |

FOREIGN PATENT DOCUMENTS 2053220  2/1981  United Kingdom.

OTHER PUBLICATIONS

Sheehan et al., J. Org. Chem., 42, pp. 4045-4048 (1977).

*Primary Examiner*—Natalie Trousof
*Assistant Examiner*—Vera C. Clarke
*Attorney, Agent, or Firm*—Charles J. Knuth; Albert E. Frost; Robert K. Blackwood

[57] ABSTRACT beta-Lactamase inhibitors which are 6-alpha- and 6-beta(aminomethyl)pencillanic acid 1,1-dioxides which are substituted on amino nitrogen with benzyl, hydroxybenzyl, picolyl or phenethyl; pharmaceutically-acceptable salts thereof; conventional esters thereof hydrolyzable in vivo; pharmaceutical compositions thereof with conventional beta-lactam antibiotics; and a method of treating bacterial infections with said pharmaceutical compositions.

23 Claims, No Drawings

6-AMINOMETHYLPENICILLANIC ACID 1,1-DIOXIDE DERIVATIVES AS BETA-LACTAMASE INHIBITORS

Cross Reference to Related Applications

This application is a continuation-in-part of copending application Ser. No. 338,797, filed Jan. 11, 1982, now abandoned. Copending application, Ser. No. 388,324, now abandoned, filed concurrently, is also a continuation-in-part of the same copending application, Serial No. 338,797.

BACKGROUND OF THE INVENTION

The present invention relates to 6-alpha- and 6-beta-(aminomethyl)penicillanic acid 1,1-dioxides which are substituted on amino nitrogen with benzyl, hydroxybenzyl, picolyl or phenethyl, pharmaceutically-acceptable salts thereof and conventional esters thereof which are hydrolyzable in vivo. While some of these compounds possess antibacterial activity per se, their principle value is as beta-lactamase inhibitors. Thus they are useful in combination with conventional beta-lactam antibiotics (penicillins and cephalosporins) against microorganisms resistant or partially resistant to beta-lactam antibiotics through production of beta-lactamase enzymes. Also encompassed by the present invention are pharmaceutical compositions comprising a present beta-lactamase inhibiting compound and a known beta-lactam antibiotic; and methods of treating bacterial infections with the above pharmaceutical compositions.

Related compounds, viz, penicillanic acid, 1,1-dioxide and esters thereof readily hydrolyzable in vivo (Barth, U.S. Pat. No. 4,234,579); various 6-beta-(hydroxymethyl)penicillanic acid 1,1-dioxides and esters thereof (Kellogg, U.S. Pat. No. 4,287,181); and 6-beta-(aminomethyl)penicillanic acid (McCombie, U.S. Pat. No. 4,237,051) have been previously described as beta-lactamase inhibitors useful in combination with beta-lactam antibiotics for the treatment of bacterial infections.

U.K. Patent Application No. 2,053,220, published Feb. 4, 1981, broadly discloses beta-lactamase inhibiting compounds of the formula

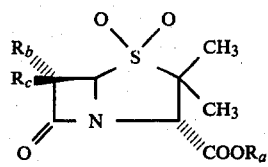

The definitions of $R_a$, $R_b$ and $R_c$ define literally an infinite number of compounds. These definitions, by appropriate selection of $R_a$, $R_b$ and $R_c$, may possibly define the simple 6-beta-(aminomethyl)- and 6-alpha-(aminomethyl)penicillanic acid 1,1-dioxides used as intermediates in the preparation of the compounds of the present invention. No specific method for preparation of these intermediate compounds is present in the disclosure of this U.K. application.

SUMMARY OF THE INVENTION

The present invention relates to compounds of the formulae

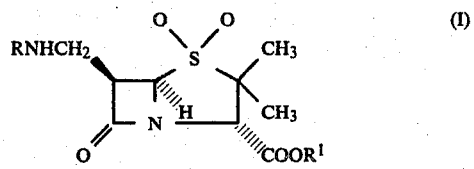

and

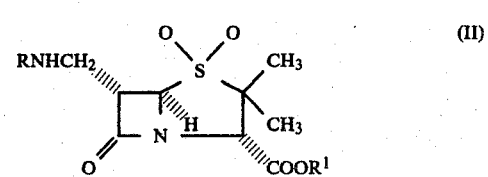

wherein
R is benzyl,
  o-, m- or -p-hydroxybenzyl, phenethyl, or
  2-, 3- or 4-picolyl; and
$R^1$ is hydrogen, or
  a radical group forming an ester which is hydrolyzable under physiological conditions;
the pharmaceutically-acceptable acid addition salts thereof; and
the pharmaceutically-acceptable cationic salts thereof when $R^1$ is hydrogen.

Pharmaceutically-acceptable acid addition salts include, but are not limited to, those with hydrochloric acid, sulfuric acid, nitric acid, phosphoric acid, citric acid, maleic acid, succinic acid, benzenesulfonic acid, p-toluenesulfonic acid, 2-naphthalenesulfonic acid and methanesulfonic acid. Pharmaceutically-acceptable cationic salts include, but are not limited to, those of sodium, potassium, calcium, N,N'-dibenzylethylenediamine, N-methylglucamine (meglumine) and diethanolamine.

The reference to esters which are hydrolyzable under physiological conditions refers to those esters frequently referred to as "pro-drugs". Such esters are now as well-known and common in the penicillin art as pharmaceutically-acceptable salts. Such esters are generally used to enhance oral absorption, but in any event are readily hydrolyzed in vivo to the parent acid. Preferred esters show no tendency to hydrogenolyze under the conditions preferably employed for their preparation (see below). The more preferred ester forming radicals are:
  gamma-butyrolacton-4-yl,
  —$CHR^2OCOR^3$, and
  —$CHR^2OCOOR^3$,
wherein $R^2$ is hydrogen or methyl and $R^3$ is ($C_1$-$C_6$)alkyl. The most preferred radicals are pivaloyloxymethyl and 1-ethoxycarbonyloxyethyl.

The preferred values of R are benzyl, phenethyl, 4-pyridyl or m-hydroxybenzyl, regardless of the value of $R^1$. Both the 6-beta-compounds (I) and the 6-alpha-compounds (II) are potent beta-lactamase inhibitors.

The compounds of the formulae (I) and (II) are useful as inhibitors of beta-lactamase enzymes. By this mechanism, these compounds enhance the activity of beta-lactam antibiotics (penicillins and cephalosporins), particularly against those microorganisms which are resistant or partially resistant to the beta-lactam antibiotic through the production of enzymes (beta-lactamases) which would otherwise destroy or partially destroy the beta-lactam antibiotic. In this manner, the spectrum of activity of the beta-lactam antibiotic is increased.

The beta-lactam antibiotics are one of the most well-known and widely-used class of antibacterial agents. These compounds are characterized by a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. While the present compounds are effective in enhancing the activity of beta-lactam antibiotics in general, their preferred use is found in their combination with a penicillin or cephalosporin of established clinical utility, viz, amoxicillin, ampicillin, azlocillin, bacampicillin, carbenicillin, carbenicillin indanyl, carbenicillin phenyl, cefaclor, cefadroxil, cefaloram, cefamandole, cefamandole nafate, cefaparole, cefatrizine, cefazoline, cefonicid, cefmenoxime, cefodizime, cefoperazone, ceforanide, cefotaxime, cefoxitin, cefsulodin, ceftazidime, ceftizoxime, ceftriaxone, cefuroxime, cephacetrile, cephalexin, cephaloglycin, cephaloridine, cephalothin, cephapirin, cephradine, cyclacillin, epicillin, hetacillin, levopropylcillin, mecillinam, mezlocillin, penicillin G, penicillin V, phenethicillin, piperacillin, pirbenicillin, pivampicillin, sarmoxicillin, sarpicillin, suncillin, talampicillin and ticarcillin, including the pharmaceutically-acceptable salts thereof. The names employed for these beta-lactams are generally USAN, i.e., United States Adopted Names.

Although the compounds of the present invention can be administered separately from the beta-lactam antibiotic, combination dosage forms are preferred. The pharmaceutical composition, whether for oral or parenteral use, comprises in a ratio of 1:3 to 3:1 by weight a beta-lactamase inhibitor of the formula (I) or (II) and a beta-lactam antibiotic, in total amounts sufficient to successfully treat a bacterial infection in a mammal in a single or, more usually, multiple dosage.

Intermediates employed for the synthesis of compounds of the present invention have the following stereochemical formulae

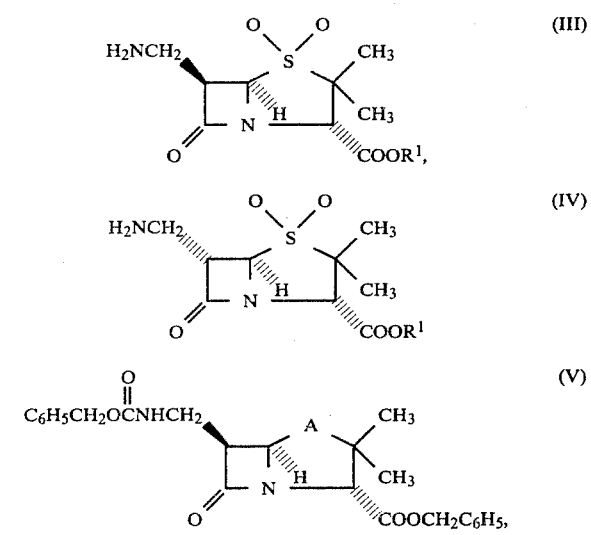

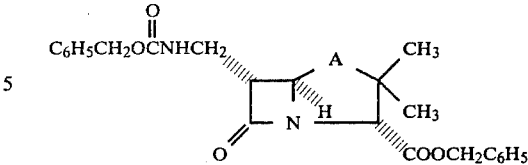

wherein A is

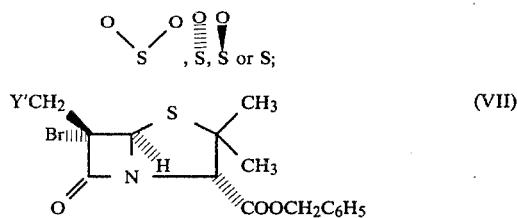

and

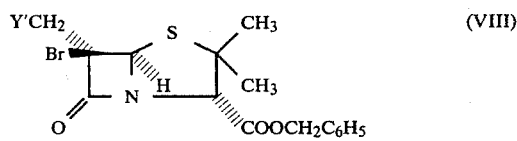

wherein Y' is benzyloxycarbonylamino,
amino,
azido or
trifluoromethanesulfonyloxy.

DETAILED DESCRIPTION OF THE INVENTION

The compounds of the formulae (I) and (II) are readily prepared by reductive alkylation of the simple 6-(aminomethyl) compounds of the above formulae (III) and (IV), in the presence of an equimolar amount of the corresponding aldehyde, using sodium cyanoborohydride as the reducing agent. One molar equivalent of the aldehyde is fully satisfactory; an excess of sodium cyanoborohydride is generally used, e.g., about two thirds of a mole per mole of substrate. Temperature is not critical and can be in the range 0°–50° C.; conveniently ambient temperature is employed.

The required aminomethyl compounds of the formulae (III) and (IV) are generally prepared from benzyl 6,6-dibromopenicillanate or from benzyl 6-alpha-iodopenicillanate.

A preferred route, particularly for the 6-beta series, involves as a first stage conversion of the dibromo compound to an epimeric mixture of mono-Grignard reagents. This is conveniently done by an exchange reaction using essentially one molar equivalent of methyl magnesium bromide in an ether solvent (ether, tetrahydrofuran, dimethoxyethane) at low temperature (−50° to −100° C.), conveniently at −78° C., the temperature of an acetone-dry ice bath. After a brief reaction time (5–30 minutes) at such reduced temperature, the mono-Grignard reagents are contacted with essentially 0.5 molar equivalents of benzyl-oxycarboxamidomethyl acetate (usually diluted with the same ether solvent and added to the cold Grignard reagent at such a rate that the low temperature of the reaction is maintained). Reaction time is not critical; 0.5 to 2 hours at −50° to −100° C. is usually sufficient to achieve complete reaction. Mixed epimers of the above formulae (VII) and (VIII) wherein Y' is benzyloxycarbonylamino are readily recovered by acetic acid quench, concentration and chromatography. The mixture of epimers can be used directly in the next step, or if desired, separated by further column chromatography on silica gel.

The next step of the sequence is reductive removal of the bromine atom, conveniently accomplished by the action of excess tri-n-butyltin hydride, optionally in the presence of small amounts (less than 0.1 molar equivalents) of a free radical initiator such as 2,2'-azobisisobutyronitrile (AIBN). Here and hereinafter, "reaction-inert solvent" is defined as a solvent which does not react with starting materials, reagents, intermediates or products in a manner which significantly reduces the yield of the desired product. Well-suited in the present case are hydrocarbon solvents such as benzene or toluene. Temperature should be elevated (60°–100° C.), such that reaction occurs in a reasonable time, but not so high as to cause undue thermal degradation. When this step is carried out on the mixed epimer precursors, the 6 beta-epimer (V), wherein A is S, is recovered by crystallization; if desired the 6 alpha-epimer (VI, A=S) is recovered from the mother liquors by evaporation and chromatography.

A second preferred route, particularly for the 6-alpha series, is to react a cold ether solution of the Grignard reagent from benzyl 6-alpha-iodopenicillanate with benzyloxycarboxamidomethyl acetate under conditions described above. The resulting mixture of compounds (V) and (VI), wherein A is S, can be separated by column chromatography, but preferably are oxidized to 1,1-dioxides and then subjected to C-6 epimerization conditions to yield the clean alpha-epimer (VI, A=SO$_2$) as detailed below.

To form the 1-alpha and 1-beta oxides of the formulae (V) and (VI), wherein A is S ⫶⫶⫶ O or S ➝ O, the above sulfides of the formulae (V) and (VI), wherein A is S, are oxidized with substantially 1 molar equivalent of a peracid, conveniently m-chloroperbenzoic acid, in a reaction-inert solvent such as ethyl acetate at 0°–50° C. When benzyl 6-beta-(benzyloxycarbonylaminomethyl)penicillanate (V, A=S) is oxidized, the resulting alpha-oxide (V, A=S ➝ O) is isolated by crystallization, while the beta-oxide (V, A=S ⫶⫶⫶ O) is isolated from mother liquors by evaporation. If desired, other standard sulfoxide forming reagents can be used.

If desired, benzyl 6-beta-(benzyloxycarbonylaminomethyl)penicillanate 1-beta-oxide (V, A=S ➝ O) is rearranged to the corresponding 6-alpha epimer (VI, A=S ➝ O) by contacting the former with 1,5-diazabicyclo[4.3.0]non-5-ene. In like manner the 6-beta dioxide (V, A=SO$_2$) is converted to its 6-alpha epimer (VI, A=SO$_2$).

Oxidation of the sulfides (V) and (VI), wherein A is S, or further oxidation of the above sulfoxides, with excess peracid (but otherwise under conditions as generally described above for mono-oxide formation) yields the corresponding sulfones (1,1-dioxides) of the formulae (V) and (VI), wherein A is SO$_2$. If desired, other sulfone forming reagents such as KMnO$_4$ can be used.

Hydrogenolyis of the resulting benzyl 6(alpha or beta)(benzyloxycarbonylaminomethyl)penicillanate 1,1-dioxides, (V and VI, A=SO$_2$) produces the corresponding 6(alpha or beta)(aminomethyl)penicillanic acids (III and IV, R$^1$=H). Hydrogenolysis is carried out by methods well-known in the penicillin art. The substrate, in a reaction-inert solvent, is contacted with hydrogen in the presence of a noble metal catalyst, such as palladium, platinum or rhodium, optionally in the form of its oxide or a salt, or on a carrier such as carbon, an alkaline earth carbonate or alumina. Temperature is not critical (e.g. 0°–50° C.), but is preferably 25° C. or lower in order to minimize thermal degradation. Pressure can be varied over a wide range (subatmospheric to 100 atmospheres), but as a matter of convenience will generally be in the range of 1 to 7 atmospheres. The reaction inert solvent is preferably relatively low boiling so as to be readily removed by concentration in vacuo. Aqueous tetrahydrofuran is a solvent particularly well-suited for the present purpose. The preferred catalyst is palladium, supported on carbon.

To prepare an in vivo hydrolyzable ester precursor [i.e., a compound of the formulae (III) or (IV), wherein R$^1$ is a radical group forming an ester which is hydrolyzable under physiological conditions], the amino group of 6-(aminomethyl)penicillanic acid 1,1-dioxide is first protected with a benzyloxycarbonyl group, using methods well-known in the art. For example, benzyl chloroformate is added slowly to the amine in a reaction-inert solvent such as aqueous acetone or aqueous tetrahydrofuran while maintaining pH 8.0 at a temperature of 0°–35° C., preferably 0°–20° C. In this manner, compounds of the formulae (IX) and (X), wherein R$^1$ is H, are formed.

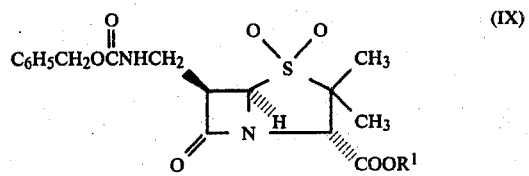

and

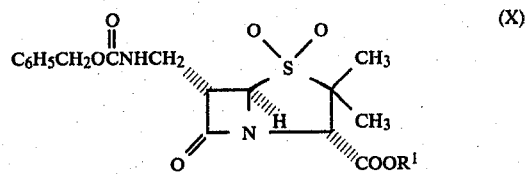

The latter intermediates are then converted to the desired esters of the formulae (IX) and (X), wherein R$^1$ now represents an in vivo hydrolyzable ester, according to known methods, readily identified by those skilled in the penicillin art (see for example U.S. Pat. Nos. 4,234,579 and 4,287,181; and European patent application No. 40494). Preferred ester values of R$^1$ have been defined above; preferred methods for the preparation of such esters are detailed in specific examples below and in European patent publication No. 40494.

The protected esters (IX) and (X) are converted to the desired esters of the formula (III) or (IV), retaining R$^1$ as the ester functionality, by hydrogenolysis according to methods described above, taking care to minimize exposure to conditions (e.g. water, lower alcohols, acids and bases) which will cause hydrolysis of the sensitive ester or beta-lactam groups.

The above-defined pharmaceutically-acceptable acid addition salts of the present invention are readily prepared by standard methods. For example, an equivalent of the acid is combined with the free amine form of the compound in an organic or aqueous organic solvent. The salt is isolated by concentration and/or the addition of a non-solvent. In some cases, the salt is isolated directly from a reaction mixture, without isolation of the free amine.

The above-defined pharmaceutically-acceptable cationic salts of those compounds of the present invention having a free carboxylic acid group are also readily prepared by standard methods. For example, an equivalent of the corresponding cationic hydroxide, carbonate or bicarbonate or of an amine is combined with the carboxylic acid in an organic or aqueous solvent, preferably at reduced temperature (e.g. 0°–5° C.), with vigorous agitation and slow addition of the base. The salt is isolated by concentration and/or the addition of a non-solvent. In some cases, the salt is isolated directly from a reaction mixture, without isolation of the free acid form.

The intermediates of the formulae (VII) and (VIII) wherein Y' is benzyloxycarbonylamino are alternatively prepared from the corresponding known benzyl 6-alpha-(hydroxymethyl)-6-beta-bromopenicillanate and benzyl 6-beta-(hydroxymethyl)-6-alpha-bromopenicillanate (also prepared from benzyl 6,6-dibromopenicillanate).

In the first stage, the above hydroxymethyl compounds are converted to the corresponding trifluoromethanesulfonate esters (VII and VIII, Y'=trifluoromethanesulfonyloxy). This reaction is conveniently carried out at room temperature using trifluoromethanesulfonic anhydride as reagent, in a reaction inert solvent such as methylene chloride in the presence of at least one equivalent of a tert-amine such as pyridine.

In the second stage the sulfonate group is displaced by azide, forming the azidomethyl compounds of the formulae (VII) and (VIII), wherein Y' is azido. An excellent reagent for this purpose is tetramethylguanidinium azide in moderate excess. The reaction is carried out at 0°–25° C., preferably about 10° C., in a reaction-inert solvent such as chloroform.

In the third stage the azido group is reduced to an amino group, yielding compounds of the formulae (VII) and (VIII) wherein Y' is amino. A convenient reagent for this purpose is hydrogen sulfide, in the presence of a tertiary amine such triethylamine in a reaction-inert solvent such as chloroform. Gaseous hydrogen sulfide is bubbled through the reaction mixture at 0°–50° C. until reduction is substantially complete.

Finally, the amino group is protected with a benzyloxycarbonyl group, using conditions standard in the art. For example benzyl chloroformate as reagent in the presence of a tertiary amine such as pyridine or N,N-diisopropylethyl amine, in a reaction-inert solvent such as methylene chloride at 0°–50° C., preferably at reduced temperature (0°–10° C.). The resulting compounds of the formulae (VII) and (VIII) wherein Y' is benzyloxycarbonylamino are then further processed according to methods detailed above.

As indicated above, some of the compounds of the formulae (I) and (II), generally those wherein $R^1$ is hydrogen, have in vitro antibacterial activity. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia Scandinav,* Supp. 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hrs. at 37° C. The susceptibility (MIC) of the test organism is accepted as the lowest concentration of compound capable of producing complete inhibition of growth as judged by the naked eye.

Those compounds of the formulae (I) and (II) having said in vitro antibacterial activity are useful as industrial antimicrobials, for example in water treatment, slime control, paint preservation and wood preservation, as well as for topical application as a disinfectant. In the case of use of these compounds for topical application, it is often convenient to admix the active ingredient with a nontoxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

As also indicated above, the compounds of the formulae (I) and (II) are of more particular value as potent inhibitors of microbial beta-lactamases. By this mechanism they increase the antibacterial effectiveness of beta-lactam antibiotics (penicillins and cephalosporins) against many microorganisms, particularly those which produce a beta-lactamase. The ability of the said compounds of the formula (I) or (II) to increase the effectiveness of a beta-lactam antibiotic can be appreciated by reference to experiments in which the MIC values of the antibiotic alone, and a compound of the formula (I) or (II) having $R^1$ as hydrogen alone are determined. These MIC's are then compared with the MIC values obtained with a combination of the given antibiotic and the compound of the formula (I) or (II), wherein $R^1$ is hydrogen. When the antibacterial potency of the combination is signficantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd Edition, 1974, American Society for Microbiology.

The compounds of the formulae (I) and (II) enhance the antibacterial effectiveness of beta-lactam antibiotics in vivo. That is, they lower the amount of the antibiotic which is needed to protect mice against an otherwise lethal inoculum of certain beta-lactamase producing bacteria In determining such activity, acute experimental infections are produced in mice by the intraperitoneal inoculation of the mice with a standardized culture of the test organism suspended in 5 percent hog gastric mucin. Infection severity is standardized so that the mice receive a lethal dose of the organism (the lethal dose is the minimum inoculum of organism required to consistently kill 100 percent of the infected, nontreated control mice). The test compound in combination with the antibiotic is administered at various dosage levels, p.o. or i.p., to groups of infected mice. At the end of the test, the activity of the mixture is assessed by counting the number of survivors among treated animals at a given dose. Activity is expressed as the percentage of animals which survive at a given dose, or calculated as a PD (dose which protects 50% of the animals from infection).

The ability of the compounds of formulae (I) and (II) to enhance the effectiveness of a beta-lactam antibiotic against beta-lactamase producing bacteria make them valuable for co-administration with beta-lactam antibiotics in the treatment of bacterial infections in mammals, particularly man. In the treatment of a bacterial infection, the compound of the formula (I) or (II) can be co-mingled with the beta-lactam antibiotic, and the two agents thereby administered simultaneously. Alternatively, the compound of the formula (I) or (II) can be administered as a separate agent during a course of treatment with a beta-lactam antibiotic. In some instances it will be advantageous to pre-dose the subject with the compound of the formula (I) or (II) before initiating treatment with a beta-lactam antibiotic.

When using a compound of formula (I) or (II) to enhance the effectiveness of beta-lactam antibiotic, a mixture of (I) or (II) with the beta-lactam antibiotic is administered preferably in formulation with standard pharmaceutical carriers or diluents. A pharmaceutical composition comprising a pharmaceutically acceptable carrier, a beta-lactam antibiotic and a compound of formula (I) or (II) will normally contain from about 5 to about 80 percent of the pharmaceutically acceptable carrier by weight.

When using the compounds of formula (I) or (II) in combination with another beta-lactam antibiotic, said compounds can be administered orally or parenterally, i.e. intramuscularly, subcutaneously or intraperitoneally. Although the prescribing physician will ultimately decide the dosage to be used in a human subject, the ratio of the daily dosages of the compounds of formula (I) or (II) and the beta-lactam antibiotic will normally be in the range from about 1:3 to 3:1 by weight. Additionally, when using the compounds of formula (I) or (II) in combination with another beta-lactam antibiotic, the daily oral dosage of each component will normally be in the range from about 10 to about 200 mg per kilogram of body weight and the daily parenteral dosage of each component will normally be about 10 to about 40 mg per kilogram of body weight. These daily doses will usually be divided. In some instances, the prescribing physician will determine that dosages outside these limits are necessary.

As will be appreciated by one skilled in the art, some beta-lactam compounds are effective when administered orally or parenterally, while others are effective only when administered by the parenteral route. When a compound of formula (I) or (II) is to be used simultaneously (i.e. co-mingled) with a beta-lactam antibiotic which is effective only on parenteral administration, a combination formulation suitable for parenteral use will be required. When a compound of formula (I) or (II) is to be used simultaneously (co-mingled) with a beta-lactam antibiotic which is effective orally or parenterally, combinations suitable for either oral or parenteral administration can be prepared. Additionally, it is possible to administer preparations of the compounds of formula (I) orally, while at the same time administering a further beta-lactam antibiotic parenterally; and it is also possible to administer preparations of the compounds of formula (I) parenterally, while at the same time administering the further beta-lactam antibiotic orally.

The present invention is illustrated by the following examples. However, it should be understood that the invention is not limited to the specific details of these examples. Unless otherwise specified, proton nuclear magnetic resonance spectra are 60 MHz.

EXAMPLE 1

Benzyl 6-alpha-bromo-6-beta-(benzyloxycarbonylaminomethyl)penicillanate and 6-beta-bromo-6-alpha-(benzyloxycarbonylaminomethyl)penicillanate To a solution of benzyl 6,6-dibromopenicillanate (108.73 g, 0.242 mole) in 600 ml dry tetrahydrofuran (THF), cooled to $-78°$ C., was added an ether solution of methyl magnesium bromide (83.5 ml of 2.9 M). After stirring for 15 minutes at $-78°$ a solution of benzyloxycarboxamidomethyl acetate (27 g, 0.121 mole) in 200 ml dry THF was added over 10 minutes. After stirring for an hour at $-78°$ the reaction was quenched by the addition of 14.52 ml of acetic acid. The mixture was warmed to room temperature and volatiles removed in vacuo at less than 35° C. Ethyl acetate was added to dissolve the residue, and the solution washed with water (100 ml), aqueous NaHCO$_3$ (100 ml), and 2×100 ml water, then dried over Na$_2$SO$_4$ and concentrated in vacuo to 113 g of oily product. The oil was column chromatographed on 1.2 kg silica gel, eluting first with 6 liters of 1:1 hexane:chloroform and then with chloroform. The first 6 liters of eluate was discarded. Further eluate was collected in 25 ml fractions. Fractions numbers 181–190 were concentrated. The pnmr spectrum of the residue in CDCl$_3$ revealed benzyl 6-alpha-bromo-6-beta-(benzyloxycarbonylaminomethyl)-penicillanate: delta/TMS 1.37 (3H, s), 1.57 (3H, s), 3.86 (2H, d, J=6 Hz), 4.42 (1H, s), 5.06 (2H, s), 5.12 (2H, s), 5.52 (1H, s), 7.25 (10H, s). Fractions numbers 201–249 were concentrated and the pnmr spectrum of this residue in CDCl$_3$ revealed benzyl 6-beta-bromo-6-alpha-(benzyloxycarbonylaminomethyl)penicillanate: delta/TMS 1.36 (3H, s), 1.60 (3H, s), 3.90 (2H, d, J=6.2 Hz), 4.47 (1H, s), 5.07 (2H, s), 5.14 (2H, s), 5.40 (1H, t, J=6.2), 5.47 (1H, s), 7.28 (5H, s), 7.30 (5H, s). The product from fractions numbers 171–240 was combined and concentrated to 22 g of foam and used in the experiment of Example 2.

EXAMPLE 2

Benzyl 6-beta-(Benzyloxycarbonylaminomethyl)penicillanate

To a solution of title products (epimeric mixture) of the preceding Example (22 g, 0.0413 mole) in 100 ml benzene was added tri-n-butyltin hydride (32.7 ml, 0.124 mole). The mixture was refluxed under N$_2$ for 2 hours, concentrated in vacuo to an oil and the oil triturated 4×100 ml hexane. The residual viscous oil was taken up in 70 ml of ether, from which title product crystallized over 1 hour [8.1 g in two crops] pnmr/CDCl$_3$/delta/TMS 1.37 (3H, s), 1.57 (3H, s), 3.58 (3H, m), 4.34 (1H, s), 5.04 (2H, s), 5.12 (2H, s), 5.33 (1H, d, J=4 Hz), 7.32 (10H, s).

Benzyl 6-alpha-(benzyloxycarbonylaminomethyl)penicillanate is recovered by concentration of mother liquors and chromatography (see Example 29).

EXAMPLE 3

Benzyl 6-beta-(Benzyloxycarbonylaminomethyl)penicillanate 1-alpha-Oxide and Benzyl 6-beta-(Benzyloxycarbonylaminomethyl)penicillanate 1-beta-Oxide To a solution of title product of the preceding Example (4.54 g, 0.01 mole) in 70 ml of ethyl acetate was added m-chloroperbenzoic acid (2.02 g, 0.01 mole) in 30 ml ethyl acetate. The mixture was stirred 30 minutes at room temperature, washed 1×50 ml saturated NaHCO$_3$ and 2×50 ml H$_2$O, dried over Na$_2$SO$_4$ and concentrated in vacuo to a viscous oil. The oil was dissolved in 50 ml of ether and 10 ml CHCl$_3$ and crystallization of title alpha-oxide induced by scratching [2.2 g, mp 123°–124° C., pnmr/CDCl$_3$/delta/TMS 1.22 (3H, s), 1.51 (3H, s), 3.7 (3H, m), 4.34 (1H, s), 4.63 (1H, d, J=4 Hz), 5.13 (2H, s), 5.22 (2H, s), 5.50 (1H, m), 7.34 (5H, s), 7.40 (5H, s)]. Concentration of mother liquor to dryness in vacuo gave the title beta-oxide as a viscous oil [2.5 g; pnmr/CDCl$_3$/delta/TMS 1.05 (3H, s), 1.60 (3H, s), 3.8 (3H, m), 4.63 (1H, s), 4.73 (1H, d, J=4 Hz), 5.13 (2H, s), 5.23 (2H, q), 5.70 (1H, m), 7.35 (5H, s), 7.39 (5H, s)].

EXAMPLE 4

Benzyl 6-alpha-(Benzyloxycarbonylaminomethyl)penicillanate 1-beta-Oxide

To title beta-oxide of the preceding Example (2.3 g, 4.9 mmoles) in 100 ml CHCl$_3$ was added 1,5-diazabicyclo[4.3.0]non-5-ene (DBN, 0.607 g, 4.9 mmoles). The mixture was stirred at room temperature for 15 minutes, diluted with 50 ml 1N HCl, and the layers separated. The organic layer was washed 2×50 ml H$_2$O, dried over Na$_2$SO$_4$ and concentrated in vacuo to an oil (2.3 g). The oil was column chromotographed on 100 g silica gel, eluting with 4:1 CHCl$_3$:ethyl acetate in 20 ml fractions. Fractions 41–70 were combined and concentrated in vacuo to yield title product as a viscous oil [0.9 g; pnmr/CDCl$_3$/TMS 1.03 (3H, s), 1.60 (3H, s), 3.67 (3H, m), 4.46 (1H, s), 4.88 (1H, m) 5.08 (2H, s), 5.17 (2H, q), 5.39 (1H, m), 7.32 (5H, s), 7.37 (5H, s)].

EXAMPLE 5

Benzyl 6-beta-(Benzyloxycarbonylaminomethyl)penicillanate 1,1-Dioxide

To a solution of title product of Example 2 (8.0 g, 0.0176 mole) in 200 ml ethyl acetate cooled to 0°–5° C. was added m-chloroperbenzoic acid (10.68 g, 0.0528 mole). The mixture was warmed to room temperature, stirred for 6 hours, recooled to 0°–5° C. and diluted with 50 ml of saturated NaHSO$_3$. The organic layer was separated, washed 2×50 ml saturated NaHCO$_3$ and 2×50 ml H$_2$O, dried over Na$_2$SO$_4$ and concentrated in vacuo to a viscous oil (8.6 g). The oil was chromatographed on 250 g. silica gel, eluting with 19:1 CHCl$_3$:ethyl acetate in 25 ml fractions. Fractions 44–150 were combined and concentrated in vacuo to yield title product as a white gummy foam [7.6 g; pnmr/CDCl$_3$/delta/TMS 1.25 (3H, s), 1.49 (3H, s), 3.98 (3H, m), 4.45 (1H, s), 4.59 (1H, d, J=4 Hz), 5.09 (2H, s), 5.19 (2H, q), 5.36 (1H, br), 7.36 (10H, s)].

EXAMPLE 6

Benzyl 6-alpha-(Benzyloxycarbonylaminomethyl)penicillanate 1,1-Dioxide

By the procedure of Example 4, the title 1,1-dioxide of the preceding Example (3.3 g, 6.79 mmoles) was converted to present title product (3.1 g crude), and purified by column chromatography on 150 g silica gel, eluting with 1:9 ethyl acetate:CHCl$_3$ in 20 ml fractions. Fractions 26–37 were combined and concentrated in vacuo to yield purified title product, as a viscous oil which crystallized on standing [1.9 g; mp 112°–113° C.; pnmr/CDCl$_3$/delta/TMS 1.20 (3H, s), 1.49 (3H, s), 3.65 (3H, m), 4.32 (1H, s), 4.59 (1H, m), 5.07 (2H, s), 5.14 (2H, q), 5.30 (1H, br), 7.32 (10H, s)].

Present title product was also obtained by the further oxidation of the title product of Example 4 with excess m-chloroperbenzoic acid according to the method of Example 5.

EXAMPLE 7

6-beta-(Aminomethyl)penicillanic Acid 1,1-Dioxide

Title product of Example 5 (1.9 g), THF (40 ml), H$_2$O (40 ml) and 10% Pd/C (1.9 g) were combined and hydrogenated at 50 psig for 1 hour. Catalyst was recovered by filtration and THF removed from the filtrate in vacuo. The aqueous layer was washed with 30 ml ethyl acetate, freeze dried to a white powder and a first crystalline crop (0.26 g) obtained by trituration of the powder with 5 ml. water. A second crop (0.14 g) crystallized on addition of 10 ml of acetone to the mother liquor and a third crop (0.35 g) by evaporating the second mother liquor to 2 ml and adding 50 ml of acetone. Total yield of title product was 0.75 g [pnmr/250 MHz/D$_2$O/delta/DSS 1.47 (3H, s), 1.59 (3H, s), 3.74 (2H, m), 4.36 (1H, td, J=4, 5.5 Hz), 4.45 (1H, s), 5.17 (1H, d, J=4 Hz)].

To obtain the potassium salt, title product (1.0 g) is dissolved in 30 ml of water and cooled in an ice water bath, one equivalent of 1N KOH is added dropwise to the well-stirred solution, and the resulting solution freeze dried.

EXAMPLE 8

6-alpha-(Aminomethyl)penicillanic Acid 1,1-Dioxide

By the method of the preceding Example, title product of Example 6 (1.7 g) was converted to present title product, except that crystalline product was obtained directly by concentration in vacuo following the ethyl acetate extraction [0.7 g; pnmr/250 MHz/D$_2$O/DSS 1.44 (3H, s), 1.59 (3H, s), 3.63 (2H, d, J=5.5 Hz) 4.07 (1H, td, J=2, 5.5 Hz) 4.31 (1H, s), 5.06 (1H, d, J=2)].

To obtain the hydrochloride salt, product (0.7 g) is dissolved in water (30 ml), an equivalent of dilute hydrochloride acid is added dropwise, and the resulting solution freeze dried.

To obtain the sodium salt, product (0.7 g) is dissolved in water (30 ml). At 0°–5° C., one equivalent of dilute sodium hydroxide is added with vigorous stirring and the solution freeze dried.

EXAMPLE 9

Benzyl 6-beta-Bromo-6-alpha-trifluoromethanesulfonyloxymethylpenicillanate

To a solution of trifluoromethanesulfonic anhydride (3.15 ml) in methylene chloride (20 ml) at room temperature was added a solution of benzyl 6-beta-bromo-6-alpha-(hydroxymethyl)penicillanate (6.232 g., 15.6 mmoles) and pyridine (1.89 ml) in methylene chloride (20 ml) and the mixture stirred and cooled in an ice bath for 45 minutes. The methylene chloride was evaporated under reduced pressure and the residue partitioned between ethyl acetate and water. The ethyl acetate phase was separated and the aqueous phase extracted with additional ethyl acetate. The combined ethyl acetate solutions were washed first with sodium bicarbonate solution at pH 8.3 and then with brine. After drying over anhydrous sodium sulfate, the solution was evaporated under reduced pressure to give title product as an orange solid [8.296 g; pnmr/CDCl$_3$/delta/TMS 1.41 (s, 3H), 1.63 (s, 3H), 4.51 (s, 1H), 4.87 (s, 2H), 5.14 (s, 2H), 5.44 (s, 1H), 7.30 (s, 5H)].

EXAMPLE 10

Benzyl 6-alpha-Azidomethyl-6-beta-bromopenicillanate

Tetramethylguanidinium azide (2.96 g, 18.7 mmoles) was added to a solution of benzyl 6-beta-bromo-6-alpha-trifluoromethylsulfonyloxymethylpenicillanate (8.296 g, 15.6 mmoles) in chloroform (50 ml) at 10° C. The reaction mixture was stirred for one hour and then reduced to one third volume and filtered through a pad of silica gel. The pad was eluted with 10% ethyl acetate/chloroform (100 ml) and the eluate evaporated to give an amber oil [6.744 g; pnmr/CDCl$_3$/delta/TMS 1.38 (s, 3H), 1.61 (s, 3H), 3.96 (s, 2H), 4.53 (s, 1H), 5.17 (s, 2H), 5.40 (s, 1H), 7.34 (s, 5H)].

EXAMPLE 11

Benzyl 6-alpha-Bromo-6-beta-trifluoromethanesulfonyloxymethylpenicillanate

Following the procedure of Example 9, benzyl 6-alpha-bromo-6-beta-hydroxymethylpenicillanate (0.548 g, 1.4 mmoles) in methylene chloride (4 ml) containing pyridine (0.17 ml) was reacted with a solution of trifluoromethanesulfonic anhdyride (0.42 ml) in methylene chloride (3 ml) to give title product as an amber oil [641 mg; pnmr/CDCl$_3$/delta/TMS 1.43 (s, 3H), 1.62 (s, 3H), 4.52 (s, 1H), 4.88 (q, 2H), 5.19 (s, 2H), 5.62 (s, 1H), 7.35 (s, 5H)].

EXAMPLE 12

Benzyl 6-alpha-Bromo-6-beta-azidomethylpenicillanate

To a solution of benzyl 6-alpha-bromo-6-beta-trifluoromethanesulfonyloxymethylpenicillanate (641 mg, 1.2 mmoles) in chloroform (10 ml) was added tetramethylguanadinium azide (229 mg, 1.2 mmoles) at 10° C. The reaction mixture was stirred for one hour and then evaporated under reduced pressure. The oily residue was filtered through a pad of silica gel and eluted therefrom with 10% ethyl acetate/chloroform. Evaporation of the eluate gave title product as an amber oil [420 mg; pnmr/CDCl$_3$/delta/TMS 1.43 (s, 3H), 1.61 (s, 3H), 3.91 (s, 2H), 4.48 (s, 1H), 5.15 (s, 2H), 5.57 (s, 1H), 7.37 (s, 5H)].

EXAMPLE 13

Benzyl 6-alpha-(Aminomethyl)-6-beta-bromopenicillanate

Hydrogen sulfide was bubbled into a rapidly stirred solution of benzyl 6-alpha-azidomethyl-6-beta-bromopenicillanate (541 mg, 1.3 mmoles) and triethylamine (0.71 ml, 4 equivalents) in chloroform (10 ml) for one hour. The reaction mixture was then evaporated in vacuo to a red oil. NMR data showed the residue to comprise the desired product contaminated with triethylamine [pnmr/CDCl$_3$/delta/TMS 1.39 (s, 3H), 1.64 (s, 3H), 3.35 (s, 2H), 4.51 (s, 1H), 5.16 (s, 2H), 5.35 (s, 1H), 7.33 (s, 5H)].

By the same method, title product of Example 12 is converted to benzyl 6-beta-(aminomethyl)-6-alpha-bromopenicillanate.

EXAMPLE 14

Benzyl 6-beta-Bromo-6-alpha-(benzyloxycarbonylaminomethyl)penicillanate

A solution of pyridine (0.14 ml) and benzyl 6-alpha-aminomethyl-6-beta-bromopenicillanate (239 mg, 0.6 mmoles) in methylene chloride (5 ml) was added via a syringe over a 5 minute period to a solution of benzylchloroformate in methylene chloride (5 ml) and the reaction mixture stirred in an ice bath under a nitrogen atmosphere for 75 minutes. The reaction mixture was evaporated in vacuo and the residue taken up in ethyl acetate/water. The pH was adjusted to 2.9 with dilute hydrochloric acid, the ethyl acetate phase separated and extracted with dilute sodium bicarbonate solution (pH 8.1), washed with brine and dried over anhydrous sodium sulfate. Evaporation under reduced pressure gave 312 mg which was taken up in chloroform and chromatographed on silica gel (15 g, 14×20 cm column) and eluted therefrom with 5% ethyl acetate/chloroform. Fractions of 4 ml each were collected. Fractions 14–27 were combined and evaporated under reduced pressure to give title product [168 mg, pnmr/CDCl$_3$/delta/TMS consistent with title product and identical with that of the same compound prepared in Example 1.

By the same method the beta-(aminomethyl) compound of the preceding Example is converted to benzyl 6-alpha-bromo-6-beta-(benzyloxycarbonylaminomethyl)penicillanate.

EXAMPLE 15

Benzyl 6-beta-(Benzyloxycarbonylaminomethyl)penicillanate

A solution of tri(n-butyl)tin hydride (0.25 ml) and benzyl 6-beta-bromo-6-alpha-(benzyloxycarbonylaminomethyl)penicillanate (168 mg, 0.31 mmoles) in benzene (4 ml) was refluxed for 2 hours. The benzene was then evaporated in vacuo and the residue triturated with hexane (3×2 ml). The remaining residue was then taken up in ethyl acetate/water, the ethyl acetate phase separated, washed with brine and dried over anhydrous sodium sulfate. Evaporation in vacuo gave 101 mg of an oil which was chromatographed on silica gel (4 g, 1×11 cm column), set up with chloroform and eluted with 5% ethyl acetate/chloroform. Fractions of 4 ml volume were collected. Fractions 3–5 were combined and evaporated to give title product (66 mg; identified by pnmr as identical with the product of Example 2).

EXAMPLE 16

6-beta-(Benzylaminomethyl)penicillanic Acid 1,1-Dioxide

To a hazy solution of the beta-aminomethyl title product of Example 7 (0.3 g, 1.145 mmoles) in 30 ml methanol was added benzaldehyde (0.117 ml, 1.145 mmoles) followed by sodium cyanoborohydride (47.6 mg, 0.758 mmole). The mixture was stirred under $N_2$ for 30 minutes at room temperature. The reaction mixture was clarified by filtration and concentrated to a foam in vacuo. The foam was dissolved in 30 ml $H_2O$, extracted 2×20 ml ethyl acetate and freeze dried to title product as a white glass (130 mg; pnmr/$D_2O$/delta/DSS 1.57 (3H, s), 1.69 (3H, s), 3.7–4.4 (5H, m), 4.38 (1H, s), 5.21 (1H, d, J=4), 7.56 (5H, s).

To obtain the hydrochloride salt, one equivalent of 1N hydrochloric acid is added dropwise prior to the freeze drying step.

To obtain the sodium salt, one equivalent of 1N sodium hydroxide is added dropwise at 0°–5° C. prior to the freeze drying step.

EXAMPLE 17

6-beta-(2-Phenylethylaminomethyl)penicillanic Acid 1,1-Dioxide

Title beta-aminomethyl product of Example 7 (0.1 g) was reacted with phenylacetaldehyde (0.098 ml) by the method of the preceding Example. The reaction mixture was concentrated in vacuo and solids recovered by trituration with 20 ml ethyl acetate. The solids were dissolved in water, the solution combined with a water extract of the ethyl acetate phase and freeze dried to yield title product [40 mg, pnmr/$D_2O$/delta/DSS 1.56 (3H, s), 1.70 (3H, s), 3.0–4.0 (6H, m), 4.28 (1H, m), 4.41 (1H, s), 5.24 (1H, d, J=4), 7.48 (5H, s)].

EXAMPLE 18

6-beta-(4-Picolylaminomethyl)penicillanic Acid 1,1-Dioxide

Title beta-aminomethyl product of Example 7 (0.1 g, 0.38 mmole) was slurried in 4 ml of water. 4-Pyridinecarbaldehyde (0.040 ml, 0.42 mmole) and then sodium cyanoborohydride (15.8 mg, 0.25 mmole) were added and the mixture stirred under nitrogen for 30 minutes at room temperature. The hazy solution was clarified, concentrated in vacuo, the residue taken up in 5 ml $H_2O$, extracted 10 ml ethyl acetate, and freeze dried to yield title product as a white glass [0.1 g; pnmr/$D_2O$/delta/DSS 1.53 (3H, s), 1.64 (3H, s), 3.3–4.1 (5H, m), 4.35 (1H, s), 5.14 (1H, d, J=4 Hz), 8.1 (4H, m)].

EXAMPLE 19

6-beta-(3-Picolylaminomethyl)penicillanic Acid 1,1-Dioxide

The procedure of the preceding Example, substituting 3-pyridinecarbaldehyde (0.039 ml) for 4-pyridinecarbaldehyde, gave present title product [70 mg, pnmr/$D_2O$/delta/DSS 1.59 (3H, s), 1.71 (3H, s), 3.7–4.5 (5H, m), 4.45 (1H, s), 5.23 (1H, d, J=4 Hz), 8.1 (4H, m)].

EXAMPLE 20

6-alpha-(Benzylaminomethyl)penicillanic Acid 1,1-Dioxide

The title alpha-aminomethyl compound of Example 8 (0.5 g, 1.91 mmoles) was reacted with benzaldehyde (0.194 ml, 1.91 mmole) and sodium cyanoborohydride (79.4 mg, 1.259 g) in a total of 26 ml of methanol according to the method of Example 16. Following the 30 minutes stir period the reaction mixture was clarified by filtration and concentrated in vacuo to a foamy residue. The residue was dissolved in 50 ml of ethyl acetate and crude product (0.45 g) precipitated by adding hexane. Crude product (0.35 g) was dissolved in 30 ml of water, extracted 2×30 ml ethyl acetate, and concentrated in vacuo to yield title product as a glass [0.28 g; pnmr/$D_2O$/delta/DSS 1.54 (3H, s), 1.67 (3H, s), 3.47 (2H, m), 4.03 (3H, m), 4.33 (1H, s), 4.98 (1H, d, J=2), 7.53 (5H, s)].

EXAMPLE 21

6-alpha-(2-Phenylethylaminomethyl)penicillanic Acid 1,1-Dioxide

The procedure of the preceding Example, substituting phenylacetaldehyde (0.446 ml) for benzaldehyde provided title product. Isolation was modified in that the crude product initially precipitated as a gum when the hexane was added to the ethyl acetate. The gum was isolated by decantation and partitioned between 20 ml ethyl acetate and 20 ml $H_2O$ and insoluble material (100 mg) removed by filtration. The aqueous layer was freeze dried to yield purified title product as a yellow solid [0.18 g, pnmr/$D_2O$/delta/DSS 1.55 (3H, s), 1.70 (3H, s), 2.9–4.0 (7H, m), 4.34 (1H, s), 5.10 (1H, d), 7.43 (5H, s)].

EXAMPLE 22

6-alpha-(4-Picolylaminomethyl)penicillanic Acid 1,1-Dioxide

The procedure of Example 20, substituting 4-pyridinecarbaldehyde (0.182 ml) for benzaldehyde gave title product. Isolation was modified in that, following filtration of the reaction mixture, the filtrate was concentrated in vacuo to a yellow foam, which was triturated with ethyl acetate, taken up in 10 ml $H_2O$ and washed with 20 ml fresh ethyl acetate. The aqueous layer was reconcentrated in vacuo to yield title product as a second yellow foam (0.38 g; pnmr/$D_2O$/delta/DSS 1.57 (3H, s), 1.70 (3H, s), 3.39 (2H, m), 4.0 (3H, m), 4.32 (1H, s), 5.01 (1H, d, J=2), 8.1 (4H, m)].

EXAMPLE 23

6-alpha-(3-Picolylaminomethyl)penicillanic Acid 1,1-Dioxide

The procedure of the preceding Example substituting 3-pyridinecarbaldehyde (0.182 ml) for 4-pyridinecarbaldehyde gave title product. Isolation was modified in that the initially isolated yellow foam was taken up in 10 ml $H_2O$, extracted 2×10 ml ethyl acetate, and the aqueous layer freeze dried to yield title product as a second yellow foam [0.39 g, pnmr/$D_2O$/delta/DSS 1.57 (3H, s), 1.70 (3H, s), 3.43 (2H, m), 4.1 (3H, m), 4.30 (1H, s), 5.00 (1H, d, J=2), 8.1 (4H, m).

EXAMPLE 24

6-alpha-(4-Hydroxybenzylaminomethyl)penicillanic Acid 1,1-Dioxide

By the procedure of the preceding Example, title product of Example 8 (0.1 g, 0.38 mmole) was reacted with 4-hydroxybenzaldehyde (46.6 mg, 0.38 ml) and sodium cyanoborohydride (15.8 mg, 0.25 mmole) in 5 ml methanol to produce freeze dried title product as a white solid [0.1 g, pnmr/$D_2O$/delta/DDS 1.53 (3H, s), 1.68 (3H, s), 3.52 (2H, m), 4.1 (3H, m), 4.33 (1H, s), 5.00 (1H, d, J=2), 7.1 (4H, m)..

EXAMPLE 25

6-alpha-(Benzyloxycarbonylaminomethyl)penicillanic Acid 1,1-Dioxide

Title product of Example 8 (2.62 g, 0.01 mole) is added to 20 ml water and 80 ml acetone at 15°–20° C., and the pH adjusted to 8 with dilute NaOH. A solution of benzyl chloroformate (1.88 g, 0.011 mole) in 20 ml acetone is added dropwise at 15°–20° C. while simultaneously maintaining the apparent pH of the reaction between 7 and 8 by the periodic addition of dilute NaOH. The reaction mixture is allowed to stir for 30 minutes, and is then concentrated in vacuo to remove most of the acetone. The aqueous solution is extracted twice with ethyl acetate and the extracts discarded. Fresh ethyl acetate (100 ml) is added to the water layer and the pH adjusted to 2 with dilute hydrochloric acid, with stirring. The organic layer is removed, washed with brine, dried over $Na_2SO_4$, and concentrated in vacuo to provide the title product. The title product of Example 7 is also converted to its N-benzyloxycarbonyl derivative by use of this acylation procedure.

EXAMPLE 26

Pivaloyloxymethyl 6-alpha-(Benzyloxycarbonylaminomethyl)penicillanate 1,1-Dioxide The title product of the preceding Example 2.3 g, 6.5 mmoles) and N,N-diisopropylethylamine (0.84 g, 6.5 mmoles) are dissolved in dimethylformamide (10 ml), chloromethyl pivalate (0.97 g, 6.5 mmoles) is added, and the mixture allowed to stir at ambient temperature for 16 hours. Ethyl ether (100 ml) is added and the mixture washed sequentially with water (4×100 ml), with 50 ml 5% aqueous hydrochloric acid, with 50 ml water, with 50 ml 5% aqueous sodium bicarbonate and with 50 ml brine before drying over $Na_2SO_4$ and evaporation in vacuo to give the title product.

The same method, but substituting an equivalent amount of bromomethyl acetate, 3-phthalidyl bromide or 1-ethoxycarbonyloxyethyl chloride, as appropriate, is used to prepare the corresponding acetoxymethyl, 3-phthalidyl and 1-ethoxycarbonyloxyethyl 6-alpha-(benzyloxycarbonylaminomethyl)penicillanate 1,1-dioxides.

By the same methods the beta epimer of the preceding example is converted to its corresponding esters.

EXAMPLE 27

Pivaloyloxymethyl 6-alpha-(Aminomethyl)penicillanate 1,1-Dioxide

Title product of the preceding Example (1 g) is hydrogenated in THF (40 ml) over 1 g of 10% Pd/C until one equivalent of hydrogen has been taken up. Catalyst is recovered by filtration and title product recovered by concentration of the filtrate in vacuo.

By the same method other esters of the preceding Example are hydrogenolyzed to yield the corresponding pivaloyloxymethyl, acetoxymethyl, 3-phthalidyl and 1-ethoxycarbonyloxyethyl ester derivatives of the acids of Examples 7 to 8.

EXAMPLE 28

Pivaloyloxymethyl 6-alpha-(Benzylaminomethyl)penicillanate 1,1-Dioxide

By the method of Example 20, title product of the preceding Example is converted to present title product.

Other amino-substituted prodrug esters are prepared from the various esters of the preceding Example according to the procedures of Examples 16–24.

EXAMPLE 29

Benzyl 6-alpha-(Benzyloxycarbonylaminomethyl)penicillanate and Benzyl 6-beta-(Benzyloxycarbonylaminomethyl)penicillanate The required Grignard agent was prepared essentially according to the method of DiNinno et al., J. Org. Chem. 42, pp. 2960–2965 (1977). Thus benzyl 6-alpha-iodopenicillanate was dissolved in 75 ml of dry tetrahydrofuran and cooled to −78° C. under dry $N_2$. Methylmagnesium bromide (5.6 ml of 3M in ether) was added dropwise. After stirring an additional 15 minutes, a solution of benzyloxycarbonylaminomethyl acetate (1.87 g) in 25 ml of dry tetrahydrofuran was added in one portion. After a second 15 minutes of stirring at −78° C., acetic acid (2 ml) was added, the mixture warmed to 0° C. and evaporated in vacuo. The residue was distributed between 250 ml ethyl acetate and 50 ml of water. The organic layer was separated, washed 1×100 ml saturated $NaHCO_3$ and 2×100 ml brine, dried over $Na_2SO_4$, and evaporated in vacuo to an oil (7.3 g). The oil was chromatographed on 250 g silica gel, eluting with 1:10 ethyl acetate:chloroform in 20 ml fractions. Fractions 20–24 contained 1.3 g of a side product (oil); fractions 25–34 contained 0.62 g of a 3:2 beta:alpha mixture of title products by pnmr assay. Fractions 35–60 contained 2.2 g of a 3:1 alpha:beta mixture of title products.

If desired the title epimers are separated by repeat chromatography of combined fractions 25–60 on 350 g of silica gel, using the same eluant.

Alternatively, fractions 25–60 are combined, then following the procedures of Examples 36, oxidized and equilibrated at C.6 to yield pure title product of Example 6.

EXAMPLE 30

Capsule

The following materials are blended to obtain a powder of uniform composition in the proportions by weight indicated below:

(a) Pivaloyloxymethyl 6-alpha-(benzylaminomethyl)-penicillanate 1,1-dioxide 1.0
(b) Ampicillin trihydrate 1.0
(c) Lactose 0.5
(d) Polyethylene glycol, average molecular weight, 4000 3.0

Blend (1375 mg) is filled into suitably sized hard gelatin capsules to obtain capsules of 250 mg potency of each active ingredient. Higher or lower potency capsules are prepared by appropriate adjustment of capsule size and fill weight. The relative weights of active ingredients are adjusted to obtain capsules wherein the weight ratio of active ingredients is other than one, e.g., the ingredients are blended in a weight ratio of 0.75, 1.5, 0.5 and 3.0, respectively, with a 1700 mg fill weight/capsule to obtain capsules having 225 mg potency of (a) and 450 mg potency of (b).

In like manner, the other beta-lactamase inhibitors of the present invention are formulated with other conventional beta-lactam antibiotics for oral use.

EXAMPLE 31

Injectable Preparation

Equal parts by weight of cefoperazone sodium and 6-beta-(benzylaminomethyl)penicillanic acid 1,1-dioxide are combined with 20 parts by weight of water and the mixture chilled to 0°–5° C. With vigorous agitation, 1N NaOH is added in a dropwise fashion in an amount just sufficient to convert the beta-lactamase inhibitor to its sodium salt. Using methods standard in the pharmaceutical art, the solution is sterile filtered, filled into vials, the vials loosely rubber stoppered, and the vials freeze dried on trays. The fill volume is such that each freeze dried vial, now sealed under vacuum, will contain 500 mg of each active ingredient. Prior to injection, each vial is made up by injection of 10 ml of sterile water for injection, through the rubber plug, and shaken to dissolve. The solution to be injected 1–10 ml is removed through the rubber plug via hypodermic needle.

What is claimed is:

1. A compound having the stereochemical formula

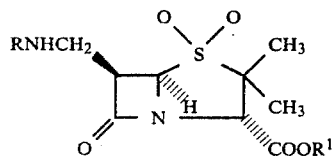
(I)

or

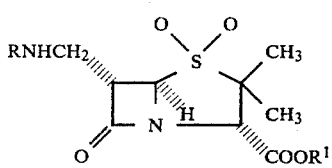
(II)

wherein
R is benzyl,
o-, m- or p-hydroxybenzyl, phenethyl, or
2-, 3- or 4-picolyl; and
$R^1$ is hydrogen, or
a radical group forming an ester which is hydrolyzable under physiological conditions;
a pharmaceutically-acceptable acid addition salt thereof or a pharmaceutically-acceptable cationic salt thereof when $R^1$ is hydrogen.

2. A compound of claim 1 wherein $R^1$ is:
gamma-butyrolacton-4-yl,
—$CHR^2OCOR^3$, or
—$CHR^2OCOOR^3$, wherein $R^2$ is hydrogen or methyl and $R^3$ is ($C_1$-$C_6$)alkyl.

3. A compound of claim 2 wherein $R^1$ is pivaloyloxymethyl.

4. A compound of claim 2 wherein $R^1$ is 1-ethoxycarbonyloxymethyl.

5. A compound of claim 1 wherein $R^1$ is hydrogen.

6. The compounds of claim 3, 4 or 5 wherein R is benzyl.

7. The compounds of claim 3, 4 or 5 wherein R is phenethyl.

8. The compounds of claim 3, 4 or 5 wherein R is 4-pyridyl.

9. The compounds of claim 3, 4 or 5 wherein R is m-hydroxybenzyl.

10. A pharmaceutical composition for treating bacterial infections which comprises, in a weight ratio of 1:3 to 3:1, a compound of claim 1 and a beta-lactam antibiotic in amounts which are effective in the treatment of bacterial infections.

11. A pharmaceutical composition of claim 10 wherein the beta-lactam antibiotic is
amoxicillin,
ampicillin,
azlocillin,
bacampicillin,
carbenicillin,
carbenicillin indanyl,
carbenicillin phenyl,
cefaclor,
cefadroxil,
cefaloram,
cefamandole,
cefamandole nafate,
cefaparole,
cefatrizine,
cefazolin,
cefmenoxime
cefonicid
cefodizime
cefoperazone,
ceforanide,
cefotaxime,
cefoxitin,
cefsulodin,
ceftazidime,
ceftizoxime,
ceftriaxone,
cefuroxime,
cephacetrile,
cephalexin,
cephaloglycin,
cephaloridine,
cephalothin,
cephapirin,
cephradine,
cyclacillin,
epicillin,
hetacillin,
levopropylcillin,
mecillinam,
mezlocillin,
penicillin G,
penicillin V,
phenethicillin,
piperacillin,
pirbenicillin,
pivampicillin, sarmoxicillin,
sarpicillin,
suncillin,
talampicillin or
ticarcillin; or
a pharmaceutically acceptable salt thereof.

12. A pharmaceutical composition of claim 11 wherein $R^1$ is hydrogen.

13. A pharmaceutical composition of claim 12 wherein R is benzyl.

14. A pharmaceutical composition of claim 12 wherein R is phenethyl.

15. A pharmaceutical composition of claim 12 wherein R is 4-pyridyl.

16. A pharmaceutical composition of claim 12 wherein R is m-hydroxybenzyl.

17. A pharmaceutical composition of claim 11, 12, 13, 14, 15 or 16 wherein the beta-lactam antibiotic is ampicillin, hetacillin, pivampicillin, bacampicillin or talampicillin.

18. A pharmaceutical composition of claim 11, 12, 13, 14, 15 or 16 wherein the beta-lactam antibiotic is amoxicillin, sarmoxicillin or sarpicillin.

19. A pharmaceutical composition of claim 11, 12, 13, 14, 15 or 16 wherein the beta-lactam antibiotic is cefoperazone.

20. A method of treating a bacterial infection in a mammal which comprises administering to said mammal an antibacterially effective amount of a pharmaceutical composition of claim 11, 12, 13, 14, 15 or 16.

21. A method of treating a bacterial infection in a mammal which comprises administering to said mammal an antibacterially effective amount of a pharmaceutical composition of claim 17.

22. A method of treating a bacterial infection in a mammal which comprises administering to said mammal an antibacterially effective amount of a pharmaceutical composition of claim 18.

23. A method of treating a bacterial infection in a mammal which comprises administering to said mammal an antibacterially effective amount of a pharmaceutical composition of claim 19.

* * * * *